(12) United States Patent
Kim (10) Patent No.: US 10,668,465 B2
(45) Date of Patent: Jun. 2, 2020

(54) COMPONENT SEPARATOR

(71) Applicant: DONGKOO BIO & PHARMA CO., LTD., Seoul (KR)

(72) Inventor: Jun-Woo Kim, Daegu (KR)

(73) Assignee: DONGKOO BIO & PHARMA CO., LTD., Seoul (KR)

( * ) Notice: Subject to any disclaimer, the term of this patent is extended or adjusted under 35 U.S.C. 154(b) by 13 days.

(21) Appl. No.: 16/037,938

(22) Filed: Jul. 17, 2018

(65) Prior Publication Data

US 2018/0318830 A1    Nov. 8, 2018

Related U.S. Application Data

(63) Continuation of application No. 15/310,817, filed as application No. PCT/KR2015/004463 on May 4, 2015, now abandoned.

(30) Foreign Application Priority Data

May 14, 2014    (KR) .................. 10-2014-0057912

(51) Int. Cl.
*B01L 3/00*    (2006.01)
*A61J 1/05*    (2006.01)
(Continued)

(52) U.S. Cl.
CPC .............. *B01L 3/50215* (2013.01); *A61J 1/05* (2013.01); *A61M 1/029* (2013.01);
(Continued)

(58) Field of Classification Search
None
See application file for complete search history.

(56) References Cited

U.S. PATENT DOCUMENTS 4,500,310 A *    2/1985    Christinger ....... A61M 5/31513
                                                    604/228
4,832,695 A      5/1989    Rosenberg et al.
(Continued)

FOREIGN PATENT DOCUMENTS

KR    10-0988221 B1    10/2010
KR    10-1179548 B1     9/2012
(Continued)

OTHER PUBLICATIONS

Notice of Preliminary Rejection for corresponding Korean Patent Application No. 10-2014-0057912, dated Sep. 26, 2014.
(Continued)

*Primary Examiner* — Matthew D Krcha
(74) *Attorney, Agent, or Firm* — Medler Ferro Woodhouse Mills PLLC (57) ABSTRACT

The present invention relates to a component separator capable of guaranteeing the purity of a subject component such as isolated blood or stem cells while simplifying a process compared with a conventional technique, and preventing air contamination during a component separation process, the component separator comprising: a hollow main body having a communication pipe, through which a body fluid communicates, formed at one end portion, and a main body female screw part disposed at the other end portion; a plunger for varying a main body space while moving forward and backward inside the main body; and an operation member having a pressing tube having a pressing male screw part capable of being screwed with the main body female screw part, and a plunger coupling tube having a tube screw screwed with a plunger screw part at the lower part of the plunger by coming into contact with or retracting from the inside of the pressing tube.

6 Claims, 10 Drawing Sheets

(51) Int. Cl.
*C12M 1/24* (2006.01)
*A61M 1/02* (2006.01)
*A61M 1/36* (2006.01)
*G01N 33/49* (2006.01)

(52) U.S. Cl.
CPC ......... *A61M 1/3693* (2013.01); *B01L 3/5021* (2013.01); *C12M 1/24* (2013.01); *A61M 1/0272* (2013.01); *A61M 2202/0427* (2013.01); *A61M 2202/0437* (2013.01); *B01L 3/5635* (2013.01); *B01L 2200/025* (2013.01); *B01L 2300/0832* (2013.01); *B01L 2300/0851* (2013.01); *B01L 2300/0858* (2013.01); *B01L 2400/0478* (2013.01); *G01N 33/491* (2013.01)

(56) References Cited

U.S. PATENT DOCUMENTS

| | | | | |
|---|---|---|---|---|
| 6,123,687 | A * | 9/2000 | Simonyi | B01D 21/245 604/207 |
| 6,171,285 | B1 * | 1/2001 | Johnson | A61M 5/322 604/110 |
| 2012/0314531 | A1 * | 12/2012 | Daub | B01F 9/0003 366/200 |
| 2013/0011311 | A1 * | 1/2013 | Kim | A61B 5/153 422/548 |
| 2013/0150803 | A1 * | 6/2013 | Shetty | A61M 5/31528 604/211 |
| 2014/0231335 | A1 | 8/2014 | Kim | |

FOREIGN PATENT DOCUMENTS

| | | |
|---|---|---|
| KR | 10-2013-0091514 A | 8/2013 |
| KR | 10-1378014 B1 | 3/2014 |

OTHER PUBLICATIONS

Decision of Patent for corresponding Korean Patent Application No. 10-2014-0057912, dated Nov. 27, 2014.
English Translation of Allowed Claims of corresponding Korean Patent Application No. 10-2014-0057912, now Korean Patent No. 10-1472821, dated Dec. 16, 2014.
International Search Report for corresponding PCT Application No. PCT/KR2015/004463, dated Jun. 30, 2015.
International Preliminary Report on Patentability for corresponding PCT Application No. PCT/KR2015/004463, dated Nov. 15, 2016.

* cited by examiner

COMPONENT SEPARATOR

FIELD OF THE INVENTION

The present invention relates to a component separator, and more specifically to a component separator capable of assuring purity of subject components such as separated blood or stem cells and preventing contamination by ambient air during the process of separating components, while simplifying the processes compared to the related art with a simple structure.

BACKGROUND OF THE INVENTION

Stem cells are used for various treatments or operation purposes. In addition, stem cells may be used for plastic or cosmetic surgery and also for the treatment of hair loss, chronic and almost incurable diseases, and pain. The scope of utilization of stem cells is considerably wide, and it is expected to expand further in the future. A stem cell refers to a cell which has the ability of self-renewal and the ability of differentiation into another cells.

Stem cells can be classified largely into embryonic stem cells and adult stem cells. In another way of classification, stem cells can be classified into autologous cells and allogenic cells. The allogenic cells may include cord blood stem cells, umbilical cord derived stem cells, placenta derived stem cells or the like. The autologous stem cells can be classified largely into bone marrow derived stem cells and adipose derived stem cells (ADSC). The main cells of these are hematopoietic stem cells (HSC) and mesenchymal stem cells (MSC). In a conventional method of separating stem cells, the extraction process progresses by the application of the extraction method in a laboratory. This process has disadvantages in that the extraction method is very fastidious, difficult to learn, and takes a lot of time; contamination can be caused by air pollution and instruments even due to slight carelessness in the extraction process; and considerable differences are made in efficiency by the extracting persons. Because of such reasons, there are needs for easy and simple methods that can also prevent contamination.

The platelet, which is one of the components of blood, contains many types of growth factors such as PDGF and TGF-BETA, which are related to wound healing. Treatment using these growth factors shows a good effect for healing skin diseases and wounds. The growth factors in these platelets are being used in the form of platelet rich plasma (PRP). When centrifugal separation is carried out, most of platelets and white blood cells are positioned in a buffy coat layer generated on an interface between blood cells and plasma. Furthermore, the plasma (platelet poor plasma (PPP)) in blood is being used for various medical purposes.

Hence, there is still a need for a more convenient and advanced method for separating the body fluid components using difference in specific gravity between cells and then extracting each component, for various medical purposes.

In particular, in the case of a adipose-derived stem cell, the quantity extracted in comparison with the volume of the whole stock solution (a mixed liquid of fat and collagenase solution) is small, so it is difficult to obtain a high-purity of stem cells by using a conventional method.

Therefore, in order to separate such body fluids, the present applicant has presented a component separator (Korean Patent Registration No. 10-1179548).

However, in the invention of the above patent, due to an external impact may occur during a separating operation, the separated components may be mixed with each other. Therefore, it is necessary to pay much attention to the operation when separating only a desired component, which may be cumbersome.

See, e.g., Korean Patent Registration No. 10-1179548.

DETAILED DESCRIPTION

Technical Problem

In consideration of the above-mentioned circumstances, it is an object of the present invention to provide a component separator capable of assuring purity of a subject component such as separated blood or stem cells and preventing contamination by ambient air during the process of separating components, while simplifying the processes compared to the related art.

Technical Solution

In order to accomplish the foregoing objects, according to an aspect of the present invention, there is provided a component separator including: a hollow main body which includes a communication pipe formed at one end portion thereof to allow a flow of body fluids therethrough and a main body female screw part disposed at the other end portion; a plunger which is installed inside of the main body to vary a main body space while moving forward and backward; and an operation member which includes a pressing tube having a pressing male screw part to be screwed with the main body female screw part, and a plunger coupling tube having a tube screw to be screwed with a plunger screw part formed at a lower part of the plunger by slidably moving inside of the pressing tube.

Herein, thread directions of the main body female screw part and the pressing male screw part may be opposite to thread directions of the plunger screw part and the tube screw.

In addition, tube screw may have an offset part formed at an end thereof without a thread.

Further, a tube protrusion stopper may be formed at a lower side of the tube screw to limit a protrusion amount of the tube screw.

Further, a tube separation preventing cover may be installed at a lower side of the pressing tube, and the plunger coupling tube may have a tube separation stopper formed at a lower portion of an outer circumference thereof to limit a movement of the plunger coupling tube.

Further, a spring may be installed between the tube separation stopper and the tube separation preventing cover to easily guide attaching and detaching of the tube screw with the plunger screw part.

Furthermore, a spring may be installed between a pressing tube protrusion formed on the pressing tube and a tube protrusion stopper of the plunger coupling tube to easily guide attaching and detaching of the tube screw with the plunger screw part.

Advantageous Effects

According to the present invention, it is possible to reduce the time and costs required in the separation work of the blood components. In particular, due to separating the blood components in an order of PPP and PRP in light specific gravity by pressing upward, it is possible to minimize or prevent mixing of blood cells, thus to reliably assure the purity of the separated PRP and PPP.

In addition, since the blood component moves in a state isolated from external air during a process of obtaining blood to a process of separating the blood components, it is possible to prevent contamination by the air. Accordingly, it is possible to prevent infection of pathogens or an occurrence of complications that may occur due to air contamination of blood in the blood separation process.

Further, separation of the stem cells may be achieved through the component separator of the present invention. In order to separate a very small quantity compared with the stock solution, the operation member is adopted so as to be able to extract high-purity stem cells in a simple manner. The operation member of a specific form allow a user to easily extract the stem cells. Thus, the costs of treatments can be reduced drastically in treatments using stem cells.

EXAMPLES

Hereinafter, exemplary embodiments of the present invention will be described in detail with reference to the accompanying drawings. Referring to the drawings, wherein like reference characters designate like or corresponding parts throughout the several views. In the embodiments of the present invention, a detailed description of publicly known functions and configurations that are judged to be able to make the purport of the present invention unnecessarily obscure are omitted.

Figure 1:
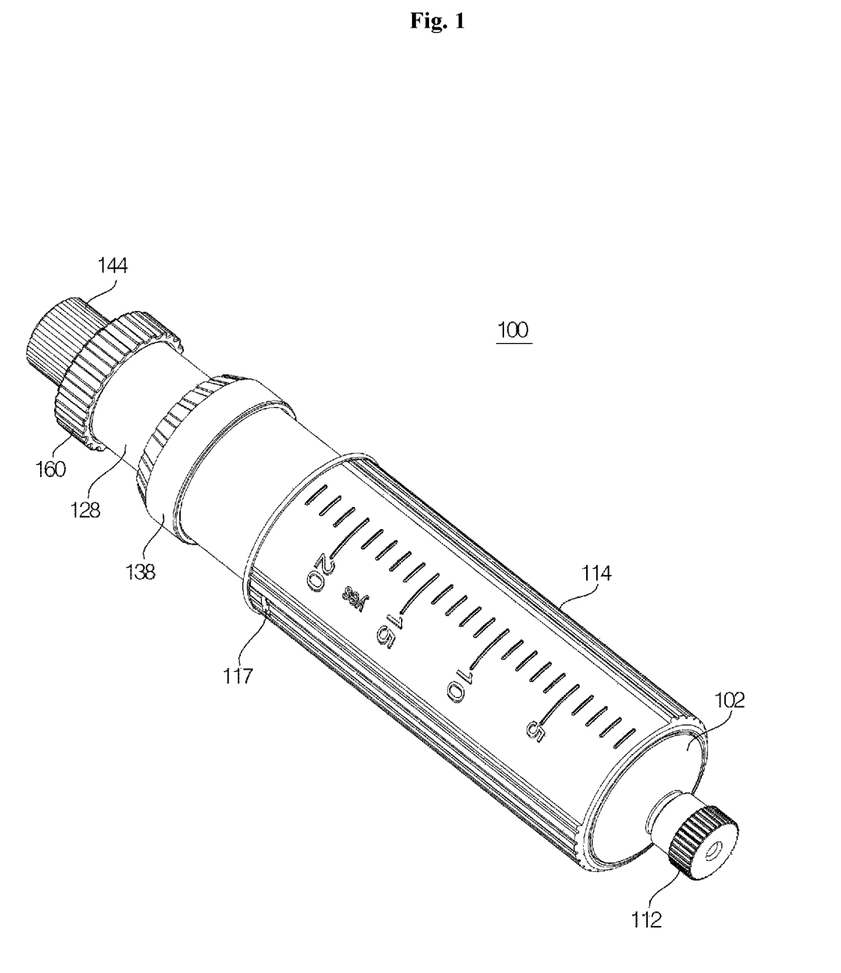
FIG. 1 is a perspective view of a component separator according to an embodiment of the present invention.
Figure 2:
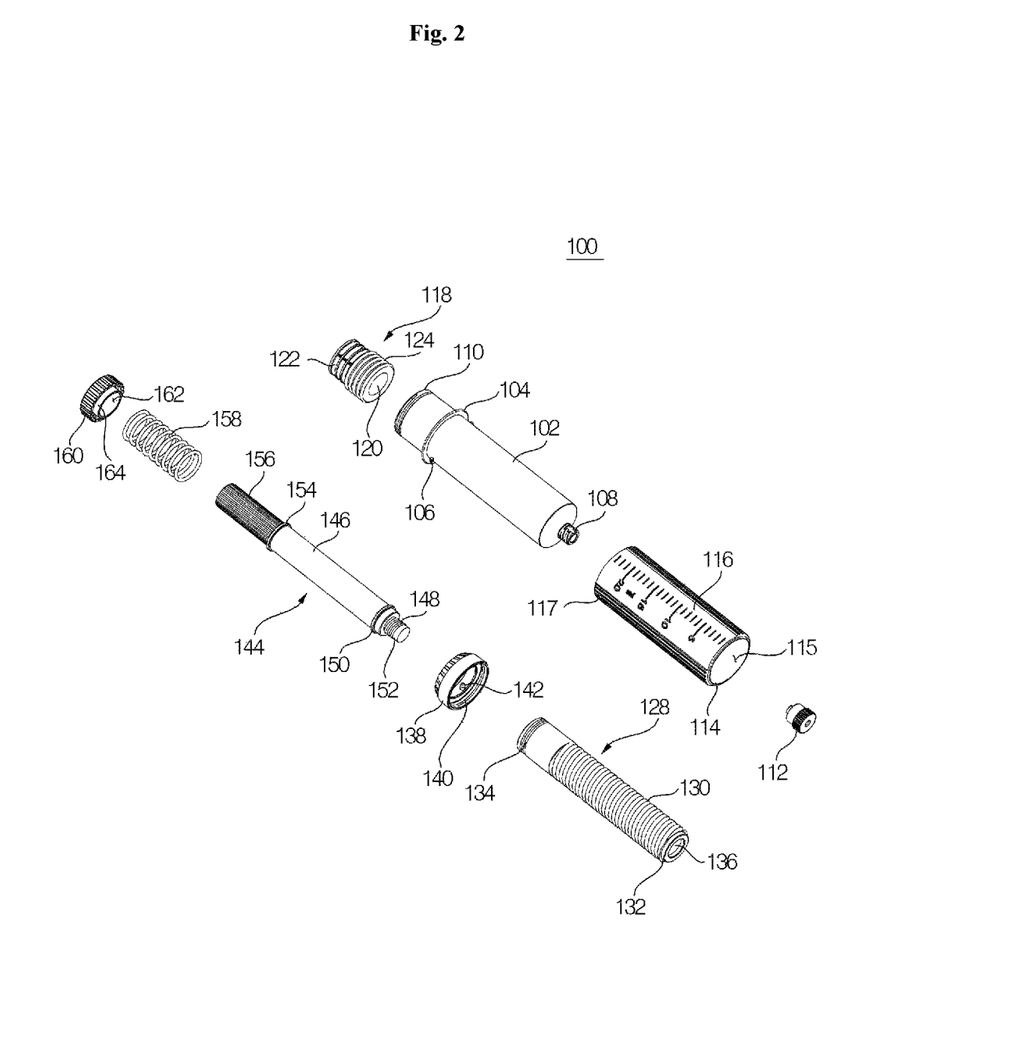
FIG. 2 is an exploded perspective view of the component separator according to the embodiment of the present invention.
Figure 3:
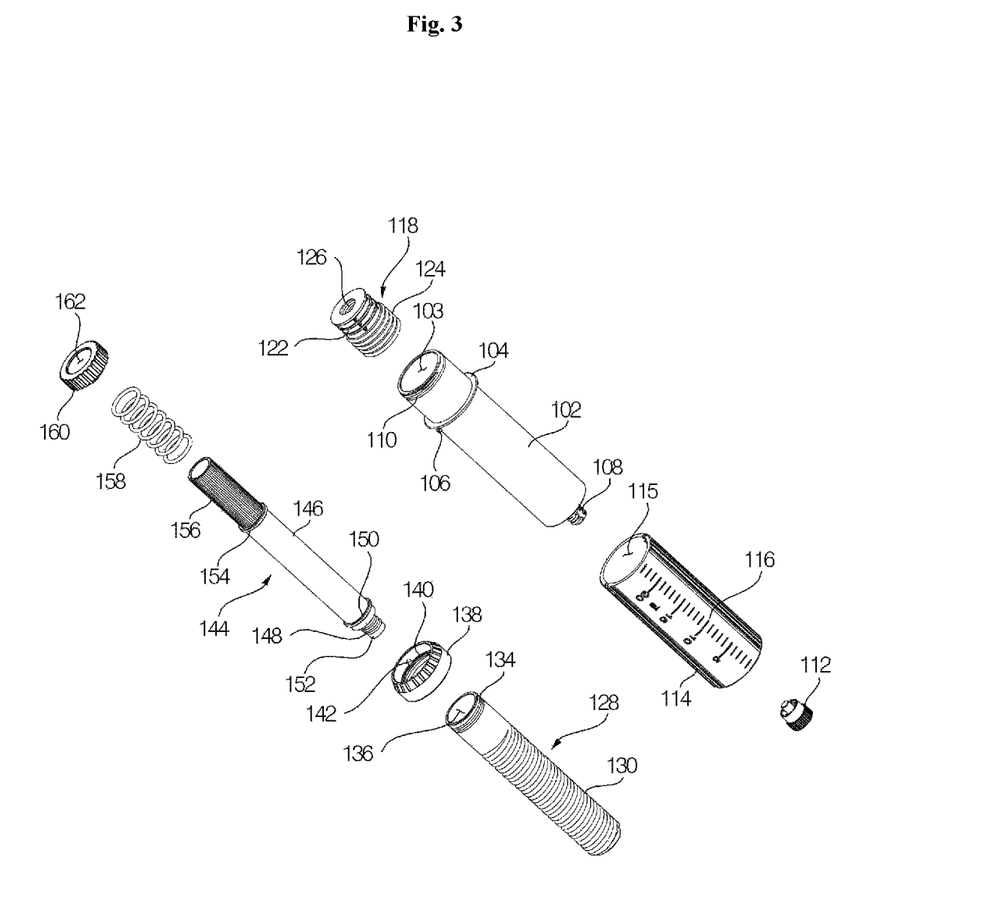
FIG. 3 is an exploded perspective view of the component separator according to the embodiment of the present invention when viewing a different direction from FIG. 2.

FIGS. 1 to 3 illustrate a component separator 100 according to an embodiment of the present invention. The component separator 100 basically includes a hollow main body 102 which has a communication pipe 108 formed at one end portion thereof to allow a flow of body fluids therethrough and a main body female screw part 142 disposed at the other end portion thereof, a plunger 118 which is installed inside of the main body 102 to vary a main body space 103 while moving forward and backward inside of the main body 102, and an operation member which pushes up the plunger 118 and pulls the plunger 118 according to circumstances.

It is preferable that the main body 102 is made of a transparent material so as to view inside thereof, and may be made of plastic or glass. The main body may be connected to other syringes through the communication pipe 108 or a communication pipe plug 112 may be coupled thereto.

The main body female screw part 142 is disposed at the other end of the main body 102. The main body female screw part 142 may be integrally formed with the main body 102, or as illustrated in the embodiment of the present invention, the main body female screw part 142 may be formed on a main body cover 138 attached and detached to and from the main body 102. The main body cover 138 detachably coupled with the main body 102 by a main body cover screw 140 which is screwed to a main body coupling screw 110 formed at a lower portion of the main body 102.

The main body female screw part 142 may be formed in a continuous thread, but as illustrated in FIGS. 2 and 3, may be formed in a protrusion form which is a portion of the thread.

The main body 102 has a main body stopper 104 formed on an outer circumference thereof, and is installed in an annular main body adapter 114 having an adapter space 115 in which the main body 102 is inserted from the communication pipe 108 side to the main body stopper 104. The main body adapter 114 is installed in order to reduce a tolerance and decrease a shake thereof, when the component separator 100 is inserted into a bucket of a centrifuge (not illustrated).

The main body adapter 114 has a scale 116 formed thereon, such that a volume of a material inside the main body 102 may be measured. Further, the main body adapter 114 has a coupling groove 117 formed on a side thereof. The coupling groove 117 is coupled with a coupling protrusion 106 formed on an outer circumference of the main body 102 by protruding therefrom. As a result, the main body adapter 114 may be placed on the main body 102.

The plunger 118 may vary a space into which body fluids, etc. are introduced inside the main body 102 while moving forward and backward inside of the main body 102. A rotational movement of the operation member is converted into a linear movement of the plunger 118. Accordingly, liquids such as body fluids may be introduced or discharged between the plunger 118 and the communication pipe 108.

Figure 4:
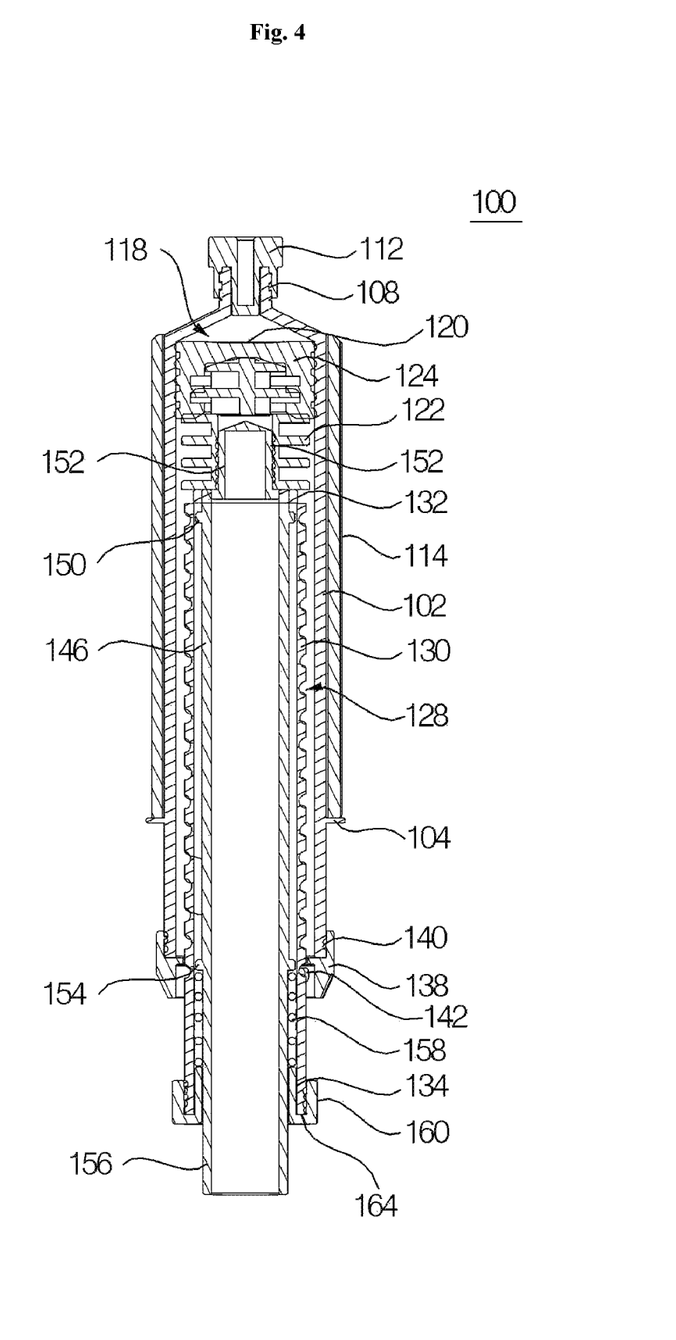
FIG. 4 is a cross-sectional view of the component separator of FIG. 1.

In addition, as illustrated in FIGS. 2 and 4, a collection part contacting with blood or body fluids may be concavely formed on an upper surface of a plunger head 124 of the plunger 118. Further, a plunger screw part 126 is formed in a center of a plunger lower portion 122 which is integrally formed with the plunger head 124. The plunger screw part 126 is screwed with a tube screw 148.

The operation member includes a pressing tube 128 having a pressing male screw part 130 that can be screwed with the main body female screw part 142, and a plunger coupling tube 144 which is screwed with the plunger screw part 126 formed at a lower part of the plunger by slidably moving inside of the pressing tube 128.

The pressing tube 128 has the pressing male screw part 130 formed on the outer circumference thereof and a pressing tube hole 136 formed in an upper portion thereof, into which the tube screw 148 of the plunger coupling tube 144 is inserted. A pressing tube protrusion 132 is disposed at a front end of the pressing male screw part 130 so as to contact with a bottom of the plunger lower portion 122. In addition, a cover coupling screw 134 may be formed at a rear end of the pressing tube 128 so as to be coupled with a tube separation preventing cover 160. Further, the spring may be installed between the pressing tube protrusion 132 of the pressing tube 128 and a tube protrusion stopper 150 of the plunger coupling tube 144.

The tube screw 148 capable of protruding through the pressing tube hole 136 is formed at a tip of the plunger coupling tube 144. The tube screw 148 is screwed with the plunger screw part 126. In addition, an offset part 152 having a size the same as or smaller than an inner diameter of the plunger screw part 126 is formed at the tip of the tube screw 148, so as to limit the movement of the plunger coupling tube 144 by inserting into the plunger screw part 126. It is preferable that the offset part 152 formed at the upper side of the tube screw 148 protrudes upward from the pressing tube protrusion 132 formed at the tip of the pressing tube 128 in a state in which the tube screw 148 is not screwed with the plunger screw part 126. That is, when moving forward the plunger 118 by rotating the pressing tube 128, the plunger operates in a state in which only the offset part 152 is simply inserted into the plunger lower portion 122 while being prevented a movement in a circumferential direction.

In addition, it is preferable that thread directions of the main body female screw part 142 and the pressing male screw part 130 are formed as opposite to thread directions of the plunger screw part 126 and the tube screw 148. For example, as illustrated in FIG. 2, it is preferable that the thread directions of the main body female screw part 142 and the pressing male screw part 130 are formed in a right-hand thread direction, the thread directions of the plunger screw part 126 and the tube screw 148 are formed in a left-hand thread direction. The reason is that, if it is necessary to push up the plunger 118 using the pressing tube 128, this operation may be performed in a state in which the plunger screw part 126 and the tube screw 148 are not screwed with each other. However, if it is necessary to pull the plunger 118 to move backward, this operation may be performed in only a state in which the plunger screw part 126 and the tube screw 148 are screwed with each other. Therefore, due to the thread directions formed as opposite to each other, when moving the plunger 118 backward, the coupling state between the plunger screw part 126 and the tube screw 148 may be maintained while preventing disengaging thereof.

In addition, in order to limit a protrusion amount of the tube screw 148, a tube protrusion stopper 150 is formed at a lower side of the tube screw 148 of a plunger coupling tube body 146. The tube protrusion stopper 150 may be formed in a loop or a protrusion shape.

A tube separation preventing cover 160 is installed at a lower side of the pressing tube 128 having a tube separation preventing cover hole 162 through which a portion of the plunger coupling tube 144 can penetrate. The plunger coupling tube 144 has a tube separation stopper 154, whose movement is limited by the tube separation preventing cover 160, formed on a lower portion of the outer circumference thereof at the lower side from the tube protrusion stopper 150. Further, in order to minimize the shake, it is preferable that outer diameters of the tube protrusion stopper 150 and the tube separation stopper 154 are the same as or slightly smaller than the inner diameter of the pressing tube hole 136, thereby reducing the tolerance thereof.

In addition, the plunger coupling tube 144 has a tube gripper 156 subjected to knurling processing at the lower portion thereof so as to facilitate rotation thereof while gripping by a hand.

A spring 158 is installed between the tube separation stopper 154 and the tube separation preventing cover 160, so as to easily guide attaching and detaching of the tube screw 148 with the plunger screw part 126. One end of the spring 158 is in contact with the tube separation stopper 154, and the other end thereof is seated on a spring seat 164 formed in the tube separation preventing cover 160. Further, both ends of the spring 158 may be directly coupled with the tube separation stopper 154 and the spring seat 164 of the tube separation preventing cover 160.

The component separator 100 according to the first embodiment of the present invention basically has the above described configuration. Hereinafter, a process for separating components using the component separator 100 will be described.

Figure 5:
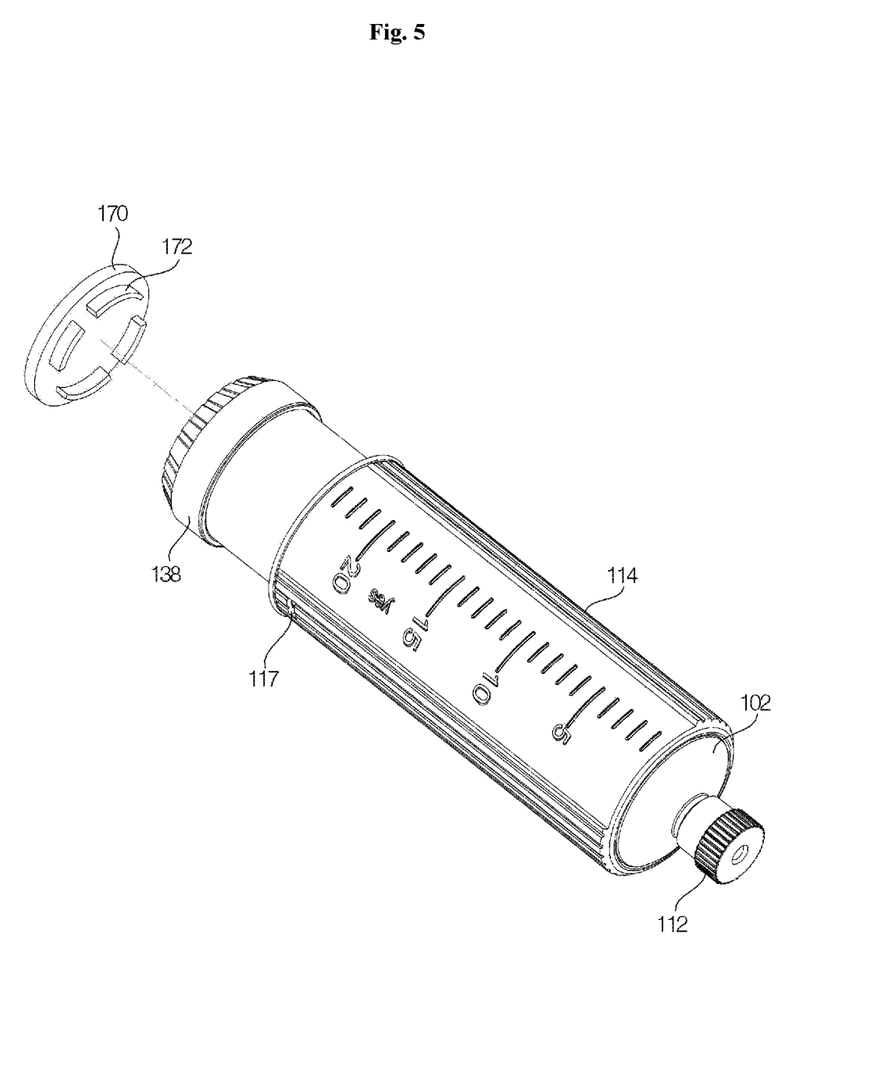
FIG. 5 is a perspective view of the component separator according to the embodiment of the present invention in a state in which an operation member is removed and a lower plug is inserted.
Figure 6:
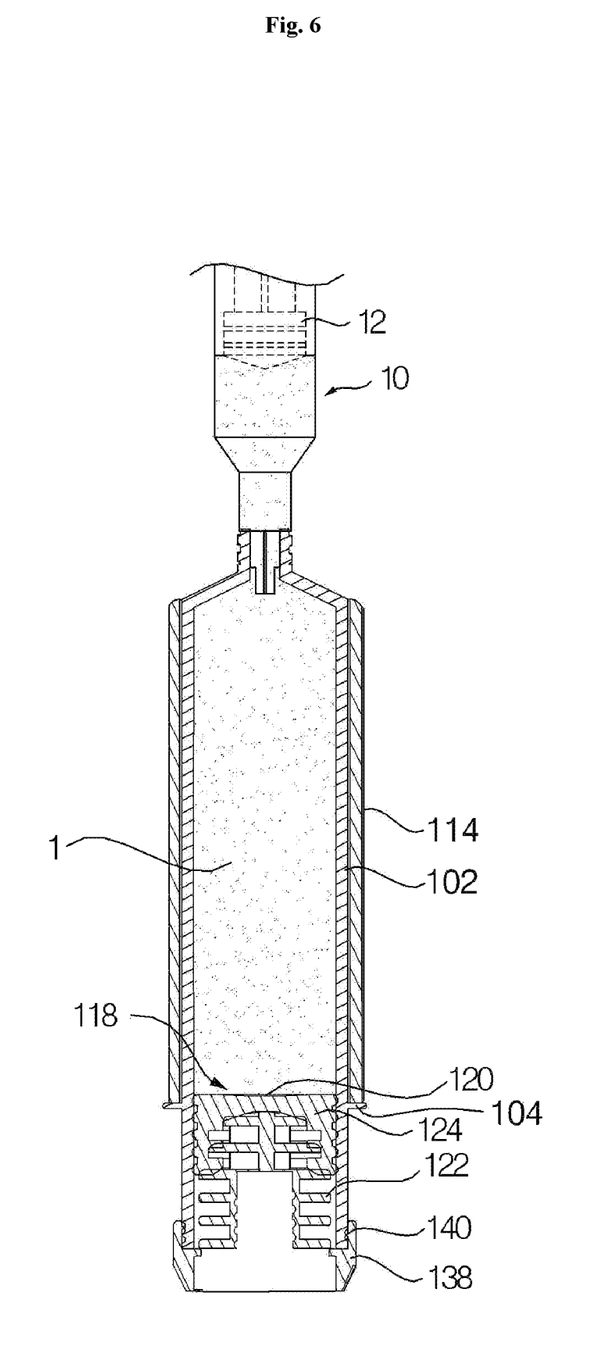
FIG. 6 is a cross-sectional view illustrating a state in which blood is introduced in the component separator of FIG. 1.
Figure 7:
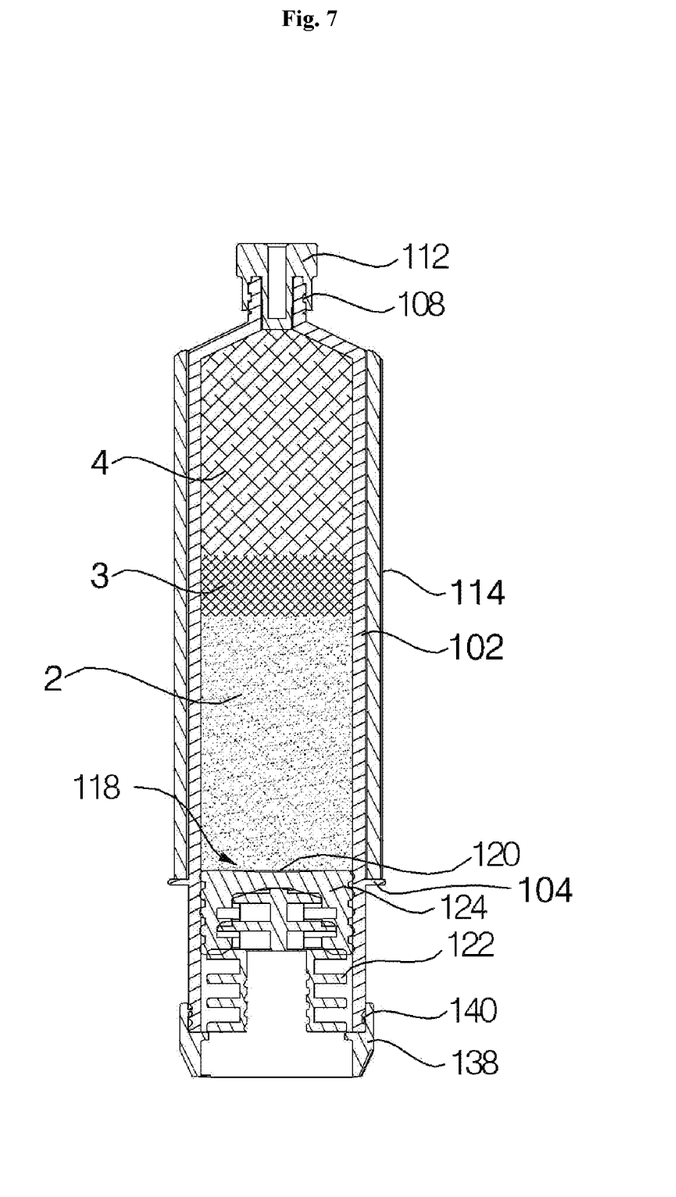
FIG. 7 is a cross-sectional view illustrating a state in which the blood introduced in the component separator of FIG. 6 is separated layer by layer using a centrifuge.

First, a process for separating blood components into PPP and PRP will be described. Plasma 4 containing a buffy coat layer 3 is referred to as a platelet rich plasma (PRP), and plasma 4 not containing the buffy coat layer 3 is referred to as a platelet poor plasma (PPP). First, blood 1 is introduced in the component separator 100 using a syringe 10, as illustrated in FIG. 6. If the component separator 100 containing the introduced blood 1 is centrifuged with being clogged by the communication pipe plug 112, the blood components are divided into blood cells 2, the buffy coat layer 3, and the plasma 4 layer by layer from the bottom layer. In this state, when performing the centrifuge, as illustrated in FIG. 5, it is possible to prevent contamination by clogging the lower portion of the main body 102 by a main body plug 170. A main body plug coupling member 172 is formed in the main body plug 170, such that the main body plug may be stably coupled to the lower portion of the main body 102.

Figure 8:
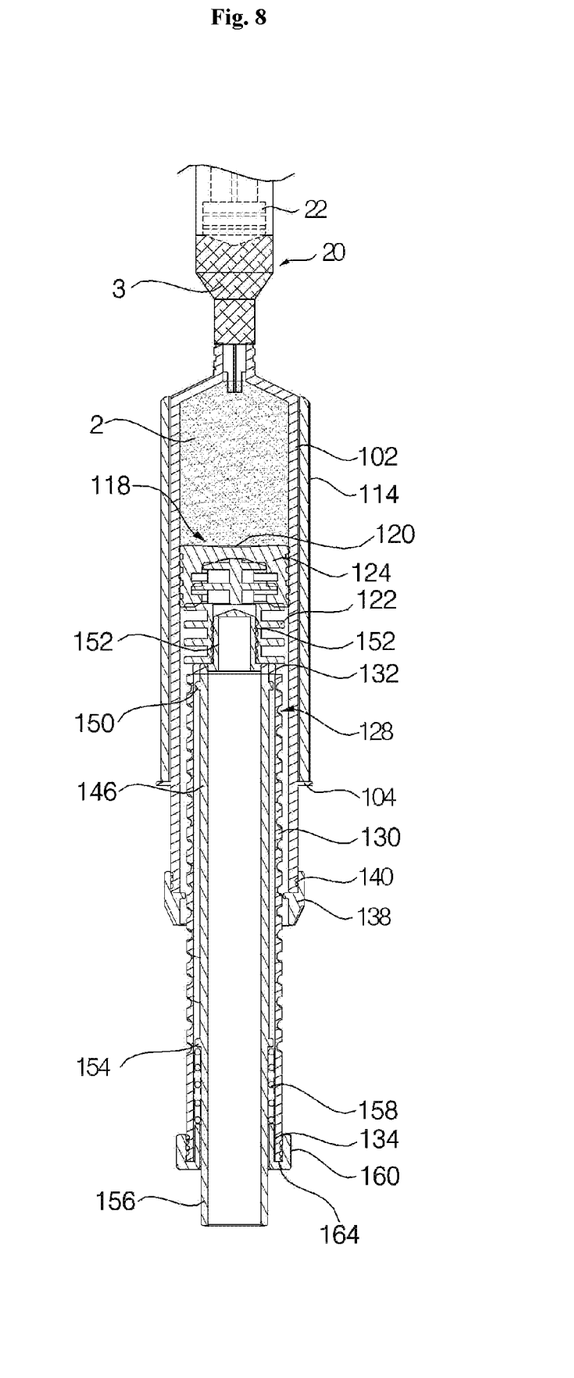
FIG. 8 is a cross-sectional view illustrating a state in which the operation member is coupled to the component separator of FIG. 7, and the operation member is raised and upper blood components of the component separator is pressed so as to supply the component to a component collector connected to the component separator.

Next, the communication pipe plug 112 is removed, and another syringe 20 is connected to the communication pipe 108, then the operation member is coupled to the lower portion of the main body 102. Thereafter, when rotating the pressing tube 128, the main body female screw part 142 and the pressing male screw part 130 are screwed with each other, and thereby the plunger 118 is raised while the pressing tube 128 is raised. In this case, the thread directions of the plunger screw part 126 and the tube screw 148 are opposite to the thread directions of the main body female screw part 142 and the pressing male screw part 130, an unscrewed state is maintained. In addition, the offset part 152 is inserted into the plunger screw part 126, such that a rotation center of the plunger screw part 126 and a rotation center of the plunger coupling tube 144 may coincide with each other while the plunger coupling tube 144 is not shaken.

As a result, the components to be separated such as the plasma 4 may be discharged toward the syringe 20. Thereafter, the above-described work may be repeatedly performed to separate a higher purity component.

Next, a method of separating adipose-derived stem cells will be described. First, in order to extract adipose-derived stem cells, fats are obtained by a method such as suction. Then, water portion is removed from the obtained fats through a decanting process or centrifugation process to obtain pure fats. Thereafter, collagenase solution in which saline water and collagenase are blended, is mixed in the obtained pure fats. Additionally, an incubation process in which stem cells existing between fat cells are allowed to be liberated sufficiently is carried out.

Then, a subject solution containing the stem cells introduced into the component separator 100 through the communication pipe 108. Alternatively, after the pure fats and the collagenase solution are mixed, the mixture is directly introduced into the component separator 100, thereby the incubation process for liberating the stem cells existing between fat cells may be carried out in the component separator 100.

Figure 9:
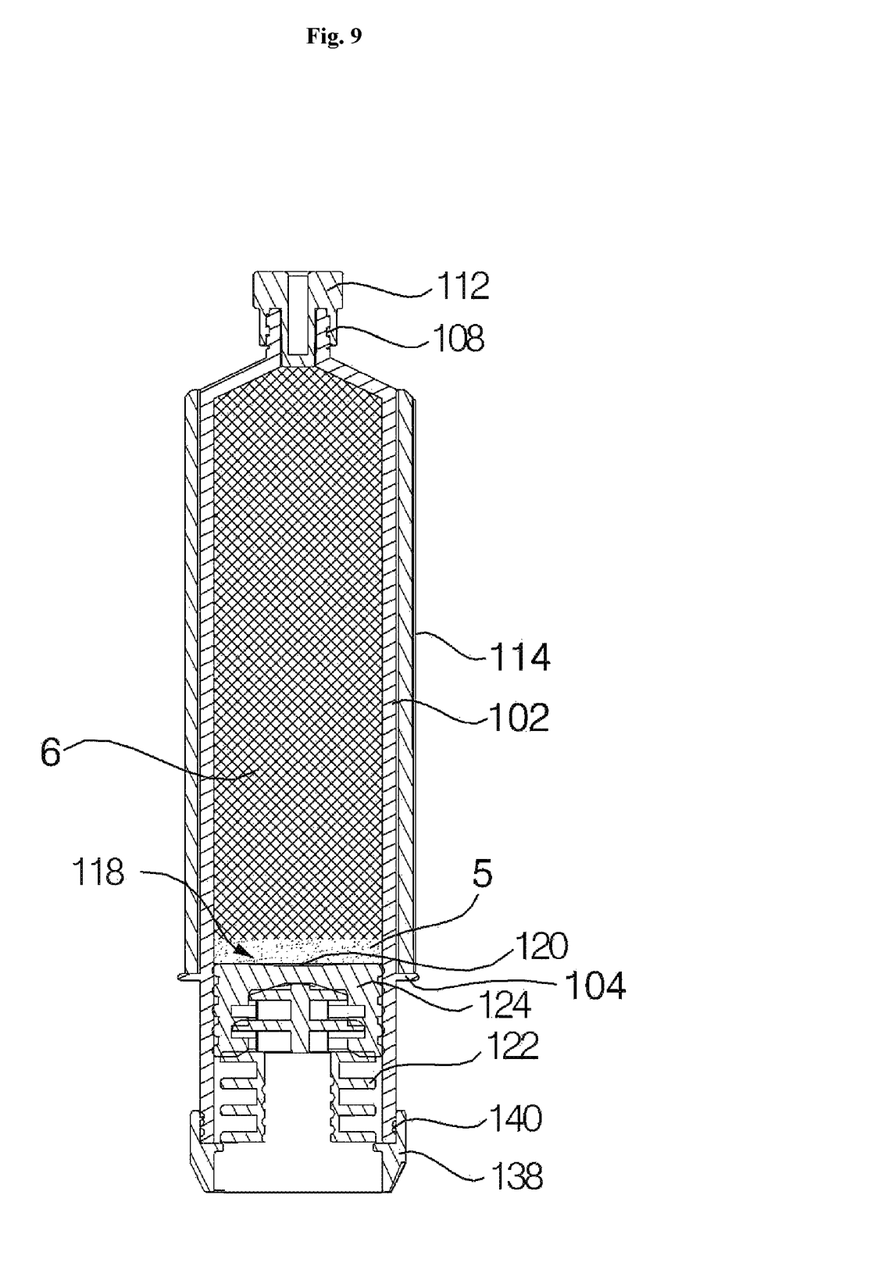
FIG. 9 is a cross-sectional view of the component separator in a state in which a mixture of pure fat and collagenase solution is separated layer by layer using the centrifuge.
Figure 10:
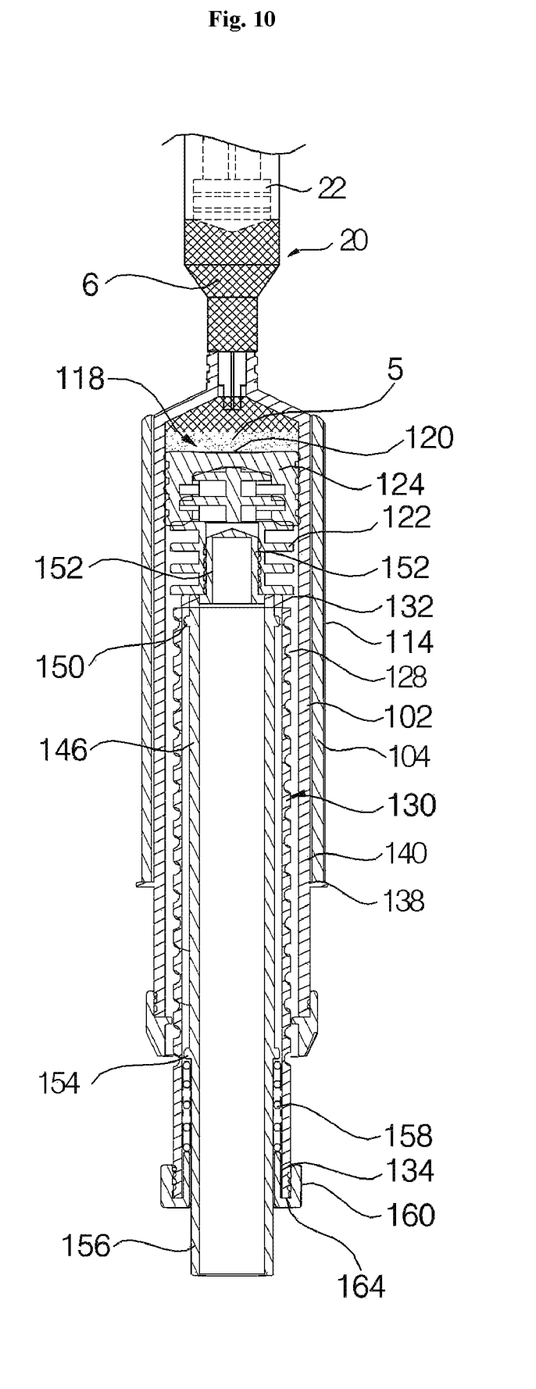
FIG. 10 is a cross-sectional view illustrating a state in which the operation member is coupled to the component separator, and the operation member is raised and upper supernatant fractions at an upper side is pressed so as to discharge to the component collector.

Then, the component separator 100 is inserted into a syringe (not illustrated) to separate the subject solution layer by layer. Consequently, as illustrated in FIG. 9, a—stem cell fraction solution 5 is arranged at the lower side, and a supernatant fraction 6 is arranged at the upper side. (Strictly speaking, a mass in which cells present in a pellet form are concentrated in a collection part 120 may refer to a stem cell fraction, and a state in which the stem cell fraction is floated on a small amount of the supernatant fraction 6 may refer to a stem cell fraction solution, for convenience of explanation, both of the stem cell fraction and a stem cell fraction solution refer to as a stem cell fraction solution). Next, as illustrated in FIG. 10, most of the supernatant fraction 6 is discharged using the operation member, and only the supernatant fraction 5 remains at the lower side.

Further, a cleaning liquid is again supplied in the component separator 100. In this case, another syringe is connected to the communication pipe 108, then the cleaning liquid is introduced into the main body 102 by pressing the syringe, or an upper syringe containing the cleaning liquid is connected to the communication pipe 108, then the cleaning liquid may be introduced by a method of moving the operation member backward. In this case, the plunger 118 is moved backward both by rotating the plunger coupling tube 144 to couple the plunger screw part 126 with the tube screw 148 and by rotating the pressing tube 128, Since the tube screw 148 and the pressing male screw part 130 have thread directions opposite to each other, even if the pressing tube 128 is rotated, the coupling state between the plunger screw part 126 and the tube screw 148 is maintained. Then, the component separator 100 containing the additionally introduced cleaning liquid is again mounted in the centrifuge, the layer separation process is performed. By repeatedly performing the above-described processes, a desired stem cell fraction solution may be finally obtained.

Next, a method of separating bone marrow-derived stem cells will be described. In the case of the bone marrow-derived stem cells, at first, bone marrow is extracted from portions such as iliac bone using a special needle for bone marrow extraction. Since bone marrow extract has an appearance similar to blood, it can be extracted by a method identical to the blood component separation method described above.

Furthermore, by using the above-described method, lymphoid cells, immune cells, cord blood stems cells, etc. can also be separated by using differences in specific gravity. That is, autologous/allogenic cells or xenogeneic cells can be separated also by using the above method in which differences in specific gravity of cells are used.

Although the present invention has been described in connection with the exemplary embodiments illustrated in the drawings, it is only illustrative. It will be understood by those skilled in the art that various modifications and equivalents can be made to the present invention. Therefore, the true technical scope of the present invention should not be defined by the appended claims.

DESCRIPTION OF REFERENCE NUMERALS

1: blood 2: blood cell
3: buffy coat layer 4: plasma
5: stem cell fraction solution
6: supernatant fraction
10, 20: syringe 12, 22: syringe plunger
100: component separator 102: main body
103: main body space 104: main body stopper
106: coupling protrusion 108: communication pipe
110: main body coupling screw 112: communication pipe plug
114; main body adapter 115: adapter space
116: scale 117: coupling groove
118: plunger 120: collection part
122: plunger lower portion 124: plunger head
126: plunger screw part 128: pressing tube
130: pressing male screw part 132: pressing tube protrusion
134: cover coupling screw 136: pressing tube hole
138: main body cover 140: main body cover screw
142: main body female screw part 144: plunger coupling tube
146: plunger coupling tube body 148: tube screw
150: tube protrusion stopper 152: offset part
154: tube separation stopper 156: tube gripper
158: spring 160: tube separation preventing cover
162: tube separation preventing cover hole 164: spring seat
170: main body plug 172: main body plug coupling member

What is claimed is:

1. A component separator comprising:
a hollow main body which includes a communication pipe formed at one end portion thereof to allow a flow of body fluids therethrough and a main body female screw part disposed at the other end portion;
a plunger which is installed inside of the main body, and a plunger screw part formed at an end portion thereof on the main body female screw part side; and
an operation member which is installed inside of the main body to move the plunger forward and backward so as to vary a main body space,
wherein the operation member comprises:
a hollow pressing tube which has a pressing male screw part formed on an outer surface thereof so as to be screwed with the main body female screw part and movably inserted inside of the main body in a rotation direction, and a pressing tube protrusion formed at an end portion thereof on the plunger side; and
a plunger coupling tube which is slidably inserted inside of the pressing tube, and has a tube screw which formed by extending so as to be screwed with the plunger screw part through a pressing tube hole formed by penetrating in the pressing tube protrusion, and
wherein thread direction of the main body female screw part and the pressing male screw part are opposite to thread directions of the plunger screw part and the tube screw;
wherein the plunger screw part and the tube screw are not screwed with each other when pushing the plunger forward, and the plunger screw part and the tube screw are screwed with each other when pulling the plunger backward.

2. The component separator according to claim 1, wherein the tube screw has an offset part formed at an end thereof without a thread.

3. The component separator according to claim 1, wherein a tube protrusion stopper is formed at a lower side of the plunger coupling tube adjacent to the tube screw to limit a protrusion amount of the tube screw.

4. The component separator according to claim 1, wherein a tube separation preventing cover is installed at a lower side of the pressing tube, and the plunger coupling tube has a tube separation stopper formed at a lower portion of an outer circumference thereof to limit a movement of the plunger coupling tube.

5. The component separator according to claim 4, wherein a spring is installed between the tube separation stopper and the tube separation preventing cover to easily guide attaching and detaching of the tube screw with the plunger screw part.

6. The component separator according to claim 4, wherein a spring is installed between the pressing tube protrusion formed on the pressing tube and a tube protrusion stopper of the plunger coupling tube to easily guide attaching and detaching of the tube screw with the plunger screw part.

* * * * *